United States Patent
Ozeki et al.

(10) Patent No.: US 7,655,146 B2
(45) Date of Patent: Feb. 2, 2010

(54) METHOD FOR FILTERING BLOOD OR BLOOD COMPONENTS USING LEUKOCYTE-REMOVING FILTER AND FILTER DEVICE

(75) Inventors: Makoto Ozeki, Tokyo (JP); Kentaro Yajima, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 525 days.

(21) Appl. No.: 11/675,275

(22) Filed: Feb. 15, 2007

(65) Prior Publication Data
US 2007/0199897 A1   Aug. 30, 2007

(30) Foreign Application Priority Data
Feb. 20, 2006 (JP) ............... 2006-042225

(51) Int. Cl.
*B01D 37/00* (2006.01)
*B01D 29/00* (2006.01)
*A61M 1/02* (2006.01)
*A61M 5/165* (2006.01)

(52) U.S. Cl. ............... 210/651; 210/321.6; 210/321.75; 210/348; 210/645; 210/650; 210/767

(58) Field of Classification Search ............... 210/321.6, 210/321.75, 348, 645, 650, 651, 767
See application file for complete search history.

(56) References Cited

U.S. PATENT DOCUMENTS

| | | | |
|---|---|---|---|
| 5,507,904 A | 4/1996 | Fisher et al. | |
| 6,221,264 B1 | 4/2001 | Ishida et al. | |
| 7,591,954 B2 | 9/2009 | Kimura et al. | |
| 2006/0184085 A1 | 8/2006 | Kimura et al. | |
| 2007/0275459 A1 | 11/2007 | Terashima et al. | |
| 2008/0011691 A1 | 1/2008 | Yamada et al. | |
| 2008/0110829 A1 | 5/2008 | Kobayashi | |

FOREIGN PATENT DOCUMENTS

EP   0526678   2/1993

(Continued)

OTHER PUBLICATIONS

English Language Abstract of JP 06-335516.

(Continued)

*Primary Examiner*—John Kim
(74) *Attorney, Agent, or Firm*—Greenblum & Bernstein, P.L.C.

(57) ABSTRACT

The method comprises providing a leukocyte-removing filter having a thickness of 9.0 mm to 9.4 mm, an air permeability pressure drop of 300 Pa to 700 Pa, and effective filtration area of 50 cm$^2$ to 70 cm$^2$ which comprises a flat and flexible container having an inlet port and an outlet port and a sheet-like leukocyte-removing-filter material with a thickness of 8.2 mm to 8.6 mm disposed to divide the container into an inlet-port side chamber and an outlet-port side chamber, providing a pair of volume restriction boards disposed outside of the inlet port side external surface and the outlet port side external surface of the flexible container, having the distance between the volume restriction boards at the portion where the volume restriction boards facing each other sandwich the leukocyte-removing filter being in a range from [thickness of leukocyte-removing filter+0.5 mm] to [thickness of leukocyte-removing filter+2.5 mm], and filtering blood or blood components through the leukocyte-removing filter under a pressure of 30 kPa to 50 kPa while restraining expansion of the flexible container occurring during filtration by means of the volume restriction boards.

12 Claims, 2 Drawing Sheets

FOREIGN PATENT DOCUMENTS

| | | |
|---|---|---|
| JP | 6-335516 | 12/1994 |
| JP | 7-67952 | 3/1995 |
| JP | 7-267871 | 10/1995 |
| JP | 8-507000 | 7/1996 |
| JP | 11-216179 | 8/1999 |
| JP | 2001-149444 | 6/2001 |
| JP | 2003-052808 | 2/2003 |
| WO | 90/15660 | 12/1990 |
| WO | 95/17236 | 6/1995 |

OTHER PUBLICATIONS

English Language Abstract of JP 07-067952.
English Language Abstract of JP 7-267871.
English Language Abstract of JP 2001-149444.
English Language Abstract of JP 2003-052808.

A

B

METHOD FOR FILTERING BLOOD OR BLOOD COMPONENTS USING LEUKOCYTE-REMOVING FILTER AND FILTER DEVICE

TECHNICAL FIELD

The present invention relates to a method for filtering blood or blood components using a leukocyte-removing filter to remove undesirable components such as aggregates, leukocytes, and the like in blood or blood components, and to a filter device. In particular, the invention relates to a filtering method and a filter device in which a volume restriction board is used to prevent swelling of the leukocyte-removing filter by using the leukocyte-removing filter comprising a flat and flexible container when filtering blood or blood components at a high flow rate using a blood pump or the like, thereby appropriately maintaining the thickness of the leukocyte-removing filter and unifying the flow rate.

BACKGROUND ART

In the field of blood transfusion, so-called leukocyte-free blood transfusion in which a blood product is transfused after removing leukocytes contained in the blood product has been widely used. This is because it was found that relatively slight side effects accompanying blood transfusion, such as headache, nausea, chill, or nonhemolytic fever reaction, or serious side effects which seriously affect a recipient, such as alloantigen sensitization, viral infection, or post-transfusion graft-versus-host disease (GVHD), are mainly caused by leukocytes contained in the blood product used for blood transfusion.

A method of removing leukocytes from the blood product is roughly classified into two kinds of methods of a centrifugation method in which leukocytes are separated and removed using a centrifuge by utilizing specific gravity difference among the blood components, and a filter method in which leukocytes are removed by using a filter material comprising a porous element such as fiber material or porous material having continuous pores. Of these, the filter method is widely used at present due to the advantages such as excellent leukocyte removal capability, easy operation, and a low cost.

A filter method, specifically, processing of leukocyte-containing liquid such as a blood product using a leukocyte-removing filter, has been performed in many cases beside the bed at the blood transfusion. In recent years, because of improving quality control of leukocyte-free products and efficiency of leukocyte removal operations, it is more common to process the blood in blood centers before storing the blood products.

Conventionally, a hard container of polycarbonate or the like filled with filter elements made from nonwoven fabric or porous material has widely been used as a leukocyte-removing filter. However, 1) since the container used in such a filter does not have steam permeability, it has been difficult to use a high-pressure vapor sterilization method, which is a widely accepted sterilization method in blood collection-separation sets. In addition, 2) when leukocytes are removed from two or more blood component products obtained by centrifugation of a whole blood using a so-called closed system in which a leukocyte-removing filter is incorporated in a blood separation set, the leukocyte-removing filter is also centrifuged together with the blood separation set. In such a case, a hard container has a risk of damaging bags and tubes, or the hard container itself may not withstand the stress during centrifugation and may collapse. As a method for solving these problems, flexible leukocyte-removing filters using a container made of a flexible material have been developed (see JP-A-6-335516, JP-A-7-67952, JP-A-7-267871 and JP-T-8-507000, for example,).

Usually, when blood is filtered through these leukocyte-removing filters, a bag containing a blood product to be filtered is placed on a location about 100 cm higher than the filter in order to filter the blood product by the action of gravity. As another demand for the leukocyte-removing filter in the market, reducing working time by processing a desired amount of blood in a short period of time has been desired in recent years.

For this reason, in addition to the method of filtering a blood product by the action of gravity which has been conventionally widely accepted, a method of filtrating blood in a shorter period of time by increasing the filtration speed of blood by feeding the blood to the leukocyte-removing filter under pressure by pumping the blood to be filtered has been studied.

In such a filtration method of feeding blood to a leukocyte-removing filter comprising a flexible container by pressurizing the blood with a pump and the like, a pressure drop arises due to resistance of the material of the leukocyte-removing filter during filtration, causing the space on the filter inlet side to be positively pressurized to expand the containers like a balloon. A force acting to rip the leukocyte-removing-filter material from the containers at the junction thereof is constantly created and such a force has a possibility of exploding the leukocyte-removing filter.

As one of the means to prevent such ripping, a method of increasing pressure resistance by housing the filter comprising a flexible container in a reinforced box or a cover made from a plastic or the like of which the volume is smaller than the volume of the filter when the filter is expanded has been proposed (WO 90/15660 pamphlet).

However, when a leukocyte-removing filter comprising a flexible container is stored in such a reinforcement box and blood is fed to the leukocyte-removing filter comprising a flexible container by a pump or the like under pressure, the leukocyte-removing-filter material is pressed against the container on the outlet port side due to a pressure drop generated by resistance of the leukocyte-removing-filter material. In such a state, a leukocyte-removing-filter material closely attaches to the outlet port side container and precludes the blood flow.

JP-A-2001-149444 discloses an invention in which the filter comprising a flexible container is stored in a hard holder. In order to prevent adhesion of the flexible container with the hard holder, projections such as ribs with a width of 1 mm to 3 mm and a height of 1 mm to 3 mm are provided on the inner surface of the holder at intervals of 2 mm to 6 mm. However, when blood is filtered at a high flow rate by being pressurized by a pump or the like using this hard holder, the outlet port side container against which the leukocyte-removing-filter material is pressed expands and comes into the clearance formed by two or more ribs provided inside the holder, but does not form a sufficient space for blood to flow between the leukocyte-removing-filter material and the outlet port side container, making it difficult to prevent the flow of blood from being inhibited.

As a method for solving the problem of filter adhesion, a method of preventing adhesion by inserting a soft polyvinyl chloride tube called a "connecting rod" between the filter material and outlet port side container (European Patent No. 0526678), a method of preventing adhesion of the leukocyte-removing-filter material with the outlet port side container by providing concavo-convex irregularities with a depth of 0.2 mm to 2 mm on the internal surface of the soft container (JP-A-11-216179), a method of inserting a screen made of nit fiber (WO 95/17236 pamphlet), and the like have been proposed. However, even when the leukocyte-removing filter comprising flexible containers is placed inside the reinforced box or holder described in WO 90/15660 pamphlet or JP-A-2001-149444 and blood is filtered at a high flow rate by being pressurized by a pump or the like, the leukocyte-removing-filter material adheres to the outlet port side container and a sufficient space through which the blood flows cannot be produced between the leukocyte-removing-filter material and the outlet port side container. It was thus found that it is difficult to prevent a flow of blood from being obstructed.

Moreover, in a filtration method in which blood is pressurized by a pump or the like and fed into a leukocyte-removing filter comprising a flexible container, a method of restricting the volume of the leukocyte-removing filter comprising a flexible container by providing a volume restriction board having a groove connecting outside of the flexible container toward the blood outlet port has been proposed as disclosed in JP-A-2003-052808. Although excellent flow characteristics of blood can be ensured according to the method described in JP-A-2003-052808, further improvement in respect of prevention of nonuniformity of blood flow within the filter, improvement of filtration efficiency, and the like has been desired.

As mentioned above, when conducting a high speed filtration method in which blood is filtered by being fed to a leukocyte-removing filter comprising flexible containers at a high flow rate by being pressurized using a pump or the like in order to filter a large amount of blood in a short period of time in conventional technology, there have been possibilities of filter breakage and a decrease in leukocyte removal capability due to inhibition and nonuniformity of a blood flow. It was difficult to simultaneously attain 1) efficiently increasing leukocyte removal capability and 2) effectively utilizing the filtration area by preventing nonuniformity of blood flow.

SUMMARY OF THE INVENTION

An object of the present invention is to solve the above-mentioned problems and to provide a method for filtering blood or blood components which simultaneously attains 1) efficiently increasing leukocyte removal capability and 2) effectively utilizing the filtration area by preventing nonuniform flow, when blood is filtered at a high flow rate by being fed to a leukocyte-removing filter comprising a flat and flexible container by being pressurized using a pump or the like, and a device using the method.

The inventors of the present invention have conducted extensive studies in order to provide a method and device for filtering blood or blood components in which the above problems are solved. As a result, the inventors have found that if a leukocyte-removing filter which comprises a flat and flexible container having an inlet port and an outlet port and a sheet-like leukocyte-removing-filter material with a thickness of 8.2 mm to 8.6 mm disposed to divide the container into an inlet-port side chamber and an outlet-port side chamber (the leukocyte-removing filter has a thickness of 9.0 mm to 9.4 mm and an air permeability pressure drop of 300 Pa to 700 Pa), and a pair of volume restriction boards disposed outside of the inlet port side external surface and the outlet port side external surface of the flexible container, facing each other so as to sandwich the leukocyte-removing filter (the distance between the volume restriction boards at the portion where the volume restriction boards face each other is in a range from [thickness of leukocyte-removing filter+0.5 mm] to [thickness of leukocyte-removing filter+2.5 mm]), are provided to restrain expansion of the flexible container occurring during filtration, and blood or blood components are filtered by the leukocyte-removing filter under a pressure of 30 kPa to 50 kPa, the leukocyte removal capability and the effective utilization rate of the filter are markedly improved, when the effective filtration area of the leukocyte-removing filter is in a range of 50 cm$^2$ to 70 cm$^2$. This finding has led to the completion of the present invention.

Therefore, according to the present invention, the following methods and devices (1) to (12) can be provided:

(1) A method for filtering blood or blood components, comprising providing a leukocyte-removing filter having a thickness of 9.0 mm to 9.4 mm, an air permeability pressure drop of 300 Pa to 700 Pa, and effective filtration area of 50 cm$^2$ to 70 cm$^2$ which comprises a flat and flexible flat container having an inlet port and an outlet port and a sheet-like leukocyte-removing-filter material with a thickness of 8.2 mm to 8.6 mm disposed to divide the container into an inlet-port side chamber and an outlet-port side chamber, providing a pair of volume restriction boards disposed outside of the inlet port side external surface and the outlet port side external surface of the flexible container, having the distance between the volume restriction boards at the portion where the volume restriction boards facing each other sandwich the leukocyte-removing filter being in a range from [thickness of leukocyte-removing filter+0.5 mm] to [thickness of leukocyte-removing filter+2.5 mm], and filtering blood or blood components through the leukocyte-removing filter under a pressure of 30 kPa to 50 kPa while restraining expansion of the flexible container occurring during filtration by means of the volume restriction boards.

(2) The method for filtering blood or blood components according to (1), wherein the viscosity of blood or blood components is 5 mPa·s to 15 mPa·s.

(3) The method for filtering blood or blood components according to (1), wherein the blood or blood components are a concentrated erythrocyte product.

(4) The method for filtering blood or blood components according to (1), wherein the flat and flexible container has Young's modulus of 7 N/mm$^2$ to 13 N/mm$^2$ and a thickness of 0.2 mm to 0.6 mm.

(5) The method for filtering blood or blood components according to (1), wherein the center of the inlet port and the center of the outlet port provided in the flat and flexible container are located on an intersection of a plane which is perpendicular to the filter material and passes through the center of the filter material, and the inlet-port side external surface or the outlet-port side external surface, the straight line which connects the center of the inlet-port and the center of the outlet-port passes through the center of the filter material, and the center of the inlet-port and the center of the outlet-port are respectively 10 mm to 15 mm apart from the center of the filter material.

(6) The method for filtering blood or blood components according to (1), wherein the volume restriction boards cover 80% to 100% of the effective filtration area of the leukocyte-removing filter.

(7) A device for filtering blood or blood components, comprising (a) a leukocyte-removing filter having a thickness of 9.0 mm to 9.4 mm, an air permeability pressure drop of 300 Pa to 700 Pa, and effective filtration area of 50 cm$^2$ to 70 cm$^2$ which comprises a flat and flexible container having an inlet port and an outlet port and a sheet-like leukocyte-removingfilter material with a thickness of 8.2 mm to 8.6 mm disposed to divide the container into an inlet-port side chamber and an outlet-port side chamber, and (b) a pair of volume restriction boards disposed outside of the inlet port side external surface and the outlet port side external surface of the flexible container, having the distance between the volume restriction boards at the portion where the volume restriction boards facing each other sandwich the leukocyte-removing filter being in a range from [thickness of leukocyte-removing filter+0.5 mm] to [thickness of leukocyte-removing filter+2.5 mm].

(8) The device according to (7), wherein the flat and flexible container has Young's modulus of 7 N/mm$^2$ to 13 N/mm$^2$ and a thickness of 0.2 mm to 0.6 mm.

(9) The device according to (7), wherein the center of the inlet port and the center of the outlet port provided in the flat and flexible container are located on an intersection of a plane which is perpendicular to the filter material and passes through the center of the filter material, and the inlet-port side external surface or the outlet-port side external surface, the straight line which connects the center of the inlet-port and the center of the outlet-port passes through the center of the filter material, and the center of the inlet-port and the center of the outlet-port are respectively 10 mm to 15 mm apart from the center of the filter material.

(10) The device according to (7), wherein the volume restriction boards cover 80% to 100% of the effective filtration area of the leukocyte-removing filter.

(11) The device according to (7), wherein a pair of the volume restriction boards is an integral structural body with a U-shaped cross-sectional configuration.

(12) The device according to (7), wherein a pair of the volume restriction boards is formed from two separate plates bonded in a secured or semi-secured state to maintain a certain space between them.

Figure 1:
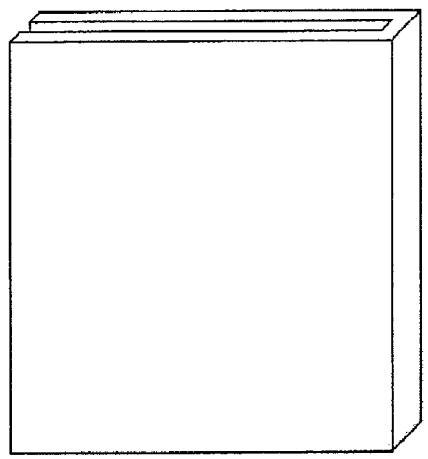
FIG. 1 shows one example of a pair of volume restriction boards (A) and another example of a pair of volume restriction boards (B).
Figure 1:
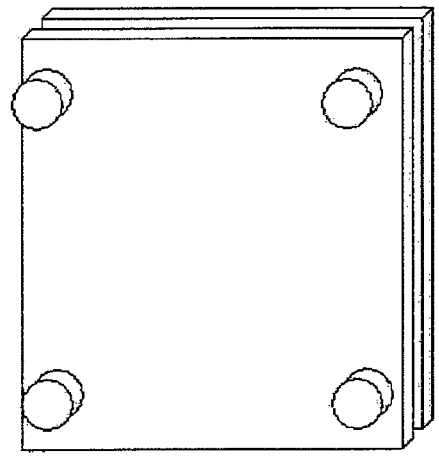

EXPLANATION OF NUMERICALS 1 leukocyte-removing filter seen from inlet port side 2 cross-section divided filter at center line parallel to longer edge of rectangle plane of filter material 3 flexible container 4 inlet port of blood or blood components 5 outlet port of blood or blood components 6 filter material 7 center of filter material (center of gravity)

8 distance between center of the filter material and inlet port of blood or blood components

DETAILED DESCRIPTION OF THE INVENTION

The present invention will be described in more detail below.

Blood components in the present invention refer to the components separated and prepared from human blood and include erythrocytes, platelets, and the like.

The leukocyte-removing filter of the present invention comprises a flat and flexible container having an inlet port and an outlet port of blood and a sheet-like leukocyte-removing-filter material disposed so as to separate the inside of the container into an outlet port side chamber and inlet port side chamber. Any filter may be used in the present invention if it is a leukocyte-removing filter made of a flat and flexible container. For example, leukocyte-removing filters made of a flat and flexible container disclosed in JP-A-6-335516, JP-A-7-67952, JP-A-7-267871, JP-T-8-507000, WO 90/15660 pamphlet, European Patent No. 0526678, JP-A-11-216179, and the like can be used in the present invention, if various special conditions described below are fulfilled.

The flexible container is preferably formed from a molded sheet made of a flexible synthetic resin. Thermoplastic elastomers such as soft polyvinyl chloride, polyurethane, an ethylene-vinyl acetate copolymer, polyolefin such as polyethylene and polypropylene, hydrogenated styrene-butadiene-styrene copolymer, styrene-isoprene-styrene copolymer or the hydrogenated product thereof, and mixtures of the thermoplastic elastomer and a softening agent such as polyolefin, ethylene-ethyl acrylate, and the like can be given as the preferable material for the flexible container. Of these, soft polyvinyl chloride, polyurethane, ethylene-vinyl acetate copolymer, polyolefin, and thermoplastic elastomer containing these polymers as the major component are preferable, with soft polyvinyl chloride and polyolefin being particularly preferable. A flexible container made from a material having Young's modulus of 7 N/mm$^2$ to 13 N/mm$^2$ and a thickness of 0.2 mm to 0.6 mm is more preferable. The Young's modulus is a ratio of a tensile stress (a load per unit area applied to a sample) to a strain corresponding thereto (elongation of the sample in the tensile direction) in a range in which the tensile stress and the strain have a linear relationship. In practice, the Young's modulus is determined by conducting a tensile test of the flexible container material using an autograph ("AG-5KNI" manufactured by Shimadzu Corp.) and a load cell ("SLBL-500N", manufactured by Shimadzu Corp.) according to JIS K7113 (Testing method for tensile properties of plastics) and calculating the inclination of a tangent at the strain starting point in the stress-strain curve using data processing software ("TRAPEZIUM" manufactured by Shimadzu Corp.).

Any flexible container can be used without specific limitations regardless of its configuration insofar as the container has a flat configuration and is provided with an inlet port of blood or blood components before filtration and an outlet port of blood or blood components after filtration. For example, the container may have a polygonal shape such as a quadrilateral or hexagonal shape or a curved shape such as a circular or elliptical shape conforming to the shape of the sheet-like leukocyte-removing-filter material. In more detail, it is preferable that the container include an inlet-side container having an inlet port for a liquid and an outlet-side container having an outlet port for the liquid. The inlet-side container and the outlet-side container directly sandwich the filter material to divide the inside of the filter into an inlet port side chamber and an outlet port side chamber for blood and blood components, thereby forming a flat leukocyte-removing filter. The leukocyte-removing filter made of a flexible container can be fabricated by sandwiching the leukocyte-removing-filter material by an inlet-port side container and an outlet-port side container and directly bonding the periphery of the leukocyte-removing-filter material with the flexible containers by welding. As the welding method, internal bonding by high frequency fusion bonding or ultrasonic welding, external bonding by heat seal, and the like can be given. The high frequency fusion bonding is desirable from the viewpoint of ensuring uniform welding.

The sheet-like leukocyte-removing-filter material refers to a fiber structure such as a nonwoven fabric manufactured by a melt-blow method, a flash spinning method, a papermaking method, or the like, a structure such as a porous material (a sponge structure) and a porous membrane having continuous pores, and a filter material capable of capturing leukocytes in blood or blood components. The sheet-like leukocyte-removing filter may include a prefilter with lower leukocyte capturing capability. The prefilter can previously remove aggregates in blood and blood components.

When the base material forming the filter material is a fiber structure, as examples of the material thereof polyamide, polyester, polyacrylonitrile, polytrifluoroethylene, polymethylmethacrylate, polyethylene, polypropylene, and the like can be given.

When a fiber structure is used as a base material, the material may comprise either a fiber having an approximately uniform fiber diameter or a mixture of two or more types of fibers having different diameters. The average fiber diameter of the fiber is preferably 0.01 μm or more and less than 3.0 μm, and the bulk density is preferably 0.1 g/cm$^3$ to 0.5 g/cm$^3$.

When the base material forming the filter material is a porous material or a porous membrane, as examples of the material thereof polyacrylonitrile, polysulfone, cellulose acetate, polyvinyl formal, polyester, polyacrylate, polymethacrylate, polyurethane, and the like can be given. Any of these materials are suitably used in the present invention. The average pore diameter of the porous material or porous membrane is preferably 1 μm or more and less than 30 μm.

The filter material may be composed from either the base material itself or a material obtained by chemically or physically modifying the surface of the base material. Either filter material is included in the leukocyte-removing-filter material with a sheet-like shape which contributes to removal of leukocytes.

The filter material may be made from a single layer of a fibrous structure, a porous material or a porous membrane or may be made from two or more layers in which these are used in combination. The area of the volume restriction board used in the method for filtering blood or blood components of the present invention may preferably be 80% or more of the effective filtration area of the leukocyte-removing filter. If the area is less than 80%, the leukocyte-removing filter portion protruding from the volume restriction board significantly swells, and unpreferably presents a risk of explosion.

The area of the volume restriction board is preferably larger than that of the leukocyte-removing filter, because the leukocyte-removing filter may be prevented from greatly expanding and improved the pressure resistance.

Any materials can be used for the volume restriction board insofar as the material can maintain the strength of the volume restriction board large enough to withstand the pressure expanding the leukocyte-removing filter, when a pressurized blood or blood components are fed to and filtered through the leukocyte-removing filter in a high flow rate. For example, as these material, hard materials such as hard plastics (e.g. polycarbonate, acryl, polystyrene, polypropylene, hard polyvinyl chloride, etc.) and a metal can be given.

In the method for filtering blood or blood components of the present invention, a pair of volume restriction boards is preferably arranged on both the inlet-port side and outlet-port side of the leukocyte-removing filter so as to sandwich the leukocyte-removing filter as shown in FIG. 1A. The volume restriction board is preferably provided with grooves and holes so that the area around the pipes of the inlet port side and outlet port side are not pressed. The surface of the volume restriction board facing the external surface of the inlet port side or the outlet port side of blood or blood components of the leukocyte-removing filter may be a smooth surface without concavo-convex irregularities or may be a concavo-convex surface having grooves, ribs, or projections with a rectangular, semicircular, or triangular cross-section. It is desirable to use two separate pieces of volume restriction boards for the inlet-port side and outlet-port side facing each other almost in parallel as shown in FIG. 1B in combination, because the distance between the two volume restriction boards can be freely adjusted.

In the present invention, "feeding and filtering blood or blood components to a leukocyte-removing filter under pressure" means an operation of pressurizing blood or blood components using a blood pump or the like, feeding the pressurized blood or blood components to the leukocyte-removing filter, and filtering the blood or blood components. Conventional filtration generally conducted under a comparatively low pressure, in which a bag containing a blood product to be processed is placed at a height about 100 cm higher than the filter to allow the blood or blood components to be filtered by gravity, differs from the filtration of filtering pressurized blood or blood components at a high flow rate in the present invention.

In the present invention, in order to pressurize blood or blood components and filter at a high flow rate, it is necessary to install a blood pump or the like between the leukocyte-removing filter and a bag containing the blood or blood components to be filtered and to feed the blood or blood components to the leukocyte-removing filter under a pressure of 30 kPa to 50 kPa. When the blood or blood components are pressurized at a pressure of less than 30 kPa, swollenness of the outlet-port side flexible container of the leukocyte-removing filter is too small to form a sufficient space between the leukocyte-removing-filter material and the outlet-port side flexible container to allow blood or blood components to flow at a high flow rate. For this reason, unpreferably the pressure drop during filtration is so large that the flow rate of the blood or blood components to be filtered is reduced. When the blood or blood components are pressurized at a pressure exceeding 50 kPa, there is unpreferably a risk of destruction of useful blood components, for example destruction of erythrocyte membrane.

The leukocyte-removing filter must have an effective filtration area of 50 cm$^2$ to 70 cm$^2$, an air permeability pressure drop of 300 Pa to 700 Pa, a thickness of 9.0 mm to 9.4 mm, and a thickness of the filter material of 8.2 mm to 8.6 mm.

The effective filtration area of the filter means the area of the leukocyte-removing filter which can be used for filtrating the blood or blood components, that is the area of the filter material in a region inside the welded portion of the flexible container and the leukocyte-removing-filter material. The effective filtration area of the leukocyte-removing filter of the present invention must be within a range of 50 cm$^2$ to 70 cm$^2$. If the effective filtration area is less than 50 cm$^2$, unpreferably the amount of the filter material which can be used for filtering leukocytes is too small to ensure sufficient leukocyte removal performance. If the effective filtration area is more than 70 cm$^2$, a considerable long time is needed for blood or blood components to permeate in the direction parallel to the filtration surface, and also a considerable long time is needed for blood or blood components to permeate the whole filter. Therefore, unpreferably the blood or blood components pass through the filter in the vertical direction of the filtration surface before permeating the whole filter, resulting in reduction of the effective utilization rate of the filter. The effective filtration area more preferably is in the range of 50 cm$^2$ to 60 cm$^2$.

An air permeability pressure drop of a leukocyte-removing filter means an index showing the resistance of the leukocyte-removing filter against an air flow. This is an index suitable for simply distinguishing the capability of a leukocyte-removing filter to accomplish a predetermined performance or not. The air permeability pressure drop of a leukocyte-removing filter in the present invention can be determined by measuring a pressure drop (Pa) generated in the filter material when the leukocyte-removing filter to be measured is placed in a sealed container and dry air is caused to flow at a constant flow rate (3.0 ml/min) while reducing the pressure outside of the filter by 40 kPa The air permeability pressure drop of a leukocyte-removing filter can be controlled by appropriately selecting and combining the filtration area of the leukocyte-removing filter, the amount of the packed filter material, diameter and meshes of fibers, and the like. The air permeability pressure drop of the leukocyte-removing filter of the present invention must be within a range of 300 Pa to 700 Pa. If less than 300 Pa, the contact area of the leukocytes with the filter material is too small to obtain sufficient leukocyte removal performance. If more than 700 Pa, the pressure drop is so large that the flow rate of the blood or blood components is unduly reduced in spite of pressurizing. A more preferable range is from 400 Pa to 600 Pa, with a still more preferable range being 450 Pa to 550 Pa.

The total thickness of a filter material is an average thickness of the filter material in the state in which all the sheets forming the filter material are laminated. In practice, the total thickness is determined by measuring the thickness of the filter material at five different points using a thickness gauge (constant pressure thickness gauge "FFA-12" manufactured by Mitsutoyo Corp.) after the filter material has been allowed to stand for 10 seconds or more under a pressure of 2 kPa (area of gauge head: 2 cm$^2$) and averaging the results. In this instance, the portion adjacent to the welded portion around the periphery of a filter material in which the thickness is reduced under compression was excluded from the area of measurement. The total thickness of the filter material in the present invention is preferably in a range of 8.2 mm to 8.6 mm. If the thickness is less than 8.2 mm, unpreferably the contact area of the filter material with blood or blood components is too small to obtain sufficient leukocyte removal capability. If the thickness is more than 8.6 mm, unpreferably the pressure drop during filtration is so large that the flow rate of the blood or blood components is unduly reduced in spite of pressurizing.

The thickness of a leukocyte-removing filter indicates the thickness of the leukocyte-removing filter including the filter material before filtering blood or blood components and can be defined by the total thickness of the filter material and the total of each of the thicknesses of flexible containers at the inlet-port side and the outlet-port side. The thickness of a flexible container is determined by measuring the thickness of a sample at five different points using a standard external micrometer defined in JIS B7502 (micrometer) and averaging the results. If the thickness of the filter is less than 9.0 mm, unpreferably the strength of the flexible container decreases so that there is a risk of breakage when blood or blood components are caused to flow under a pressure of 30 kPa to 50 kPa. If the thickness is more than 9.4 mm, the flexible container does not swell sufficiently and it takes a long time until the blood or blood components spread to the directions parallel to the filtration surface when the blood or blood components are caused to flow under pressure of 30 kPa to 50 kPa. Therefore, unpreferably the blood or blood components pass through the filter in the vertical direction of the filtration surface before permeating into the entirety of the filter, giving rise to reduction of the effective utilization rate of the filter.

The configuration and the material of the volume restriction board of the present invention is not specifically limited insofar as the volume restriction board can sandwich the leukocyte-removing filter and is strong enough to hold a certain spacing even when the containers expand during filtration. For example, an integral structural body made of plastic having a U-shaped cross-sectional configuration in which a pair of volume restriction boards facing each other is connected at one side (FIG. 1A) or a combination of two separate boards which face each other almost in parallel and connected by bolts or the like in a secured or semi-secured state so as to hold a certain space between them (FIG. 1B) can be given.

The space between the volume restriction board provided on the inlet port side and the volume restriction board provided on the outlet port side must be in a range from [thickness of leukocyte-removing filter+0.5 mm] to [thickness of leukocyte-removing filter+2.5 mm].

The space between the volume restriction boards refers to the distance between the volume restriction board used on the inlet port side and the volume restriction board used on the outlet port side of the flexible container at the portion where the volume restriction boards facing each other sandwich the leukocyte-removing filter. When the volume restriction board has concavo-convex irregularities, the space indicates the distance between end points which are the highest convex portions of the volume restriction board facing toward the external surface of the inlet port side or the outlet port side of blood or blood components If the space between the volume restriction boards on the inlet port side and the outlet port side is less than [thickness of leukocyte-removing filter+0.5 mm], the flexible container does not swell sufficiently or it takes a long time until the blood or blood components spread to the direction parallel to the filtration surface when the blood or blood components are caused to flow under a pressure of 30 kPa to 50 kPa. Therefore, unpreferably the blood or blood components pass through the filter in the vertical direction of the filtration surface before permeating the whole filter, giving rise to reduction of the effective utilization rate of the filter. On the other hand, if the space between the volume restriction boards on the inlet port side and the outlet port side is greater than [thickness of leukocyte-removing filter+2.5 mm], a large amount of blood remains in the leukocyte-removing filter after filtration, requiring an additional step for recovering the remaining blood. Therefore, unpreferably complicated operations increase, and it simultaneously takes a considerable time for the operations.

A more preferable space between the volume restriction boards is in a range from [thickness of leukocyte-removing filter+1.0 mm] to [thickness of leukocyte-removing filter+2.0 mm].

Viscosity of blood and blood components used in the present invention is measured according to the viscosity measuring method described in JIS Z 8803 (viscosity of liquid—method of measurement) using a cone plate type rotational viscometer and is determined by averaging three measurements. The viscosity of blood and blood components in the present invention is preferably in a range of 5 mPa·s to 15 mPa·s. If the viscosity of blood and blood components is less than 5 mPa·s, the concentration of blood cell components (for example, erythrocytes, platelets, etc.) which are needed for the blood or blood components is unacceptably low. Therefore, unpreferably a condensing operation is necessary in order to obtain a required concentration of blood cell components. If the viscosity of blood and blood components is greater than 15 mPa·s, unpreferably the filter may be clogged, which results in retardation of the filtration operation or stopping during the operation.

Figure 2:
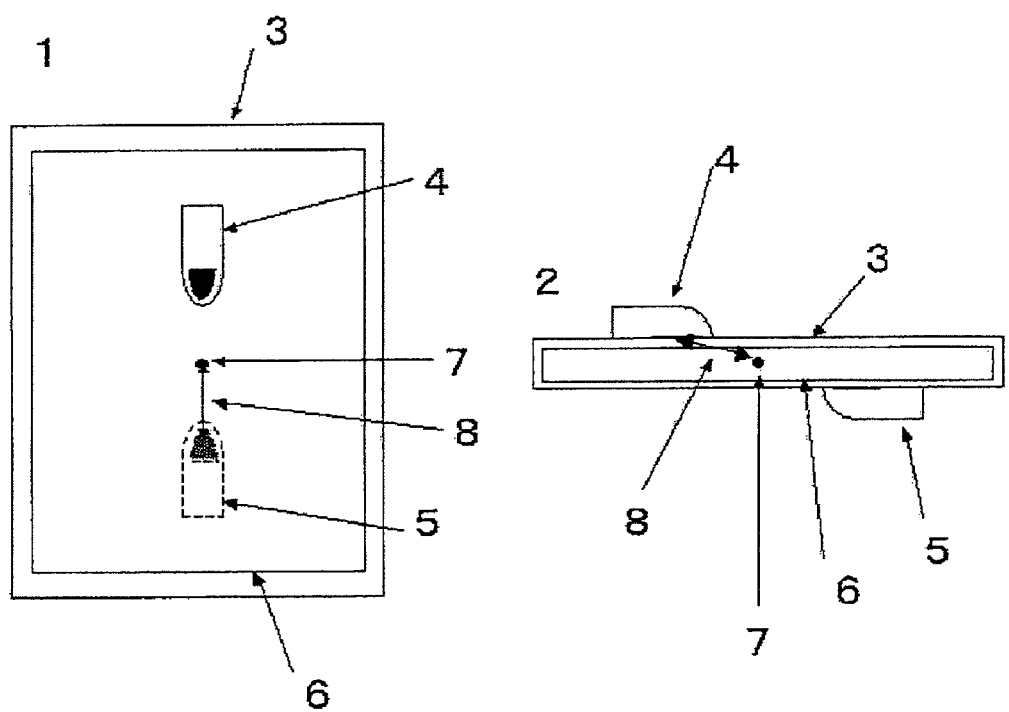
FIG. 2 shows an example of the configuration of a leukocyte-removing filter.

The structure expressed by the terms that "the inlet port provided on the inlet-port side of a flexible container and the outlet port provided on the outlet-port side are located on an intersection of a plane which is perpendicular to the filter material and passes through the center of the filter material, and the inlet-port side external surface or the outlet-port side external surface; the straight line which connects the center of the inlet-port and the center of the outlet-port passes through the center of the filter material; and the center of the inlet-port and the center of the outlet-port are respectively 10 mm to 15 mm apart from the center of the filter material" is illustrated in FIG. 2, for example, in which a leukocyte-removing filter 1 comprises a leukocyte-removing-filter material 6 in a flexible container 3, and an inlet port 4 and an outlet port 5 are arranged in the flexible container 3 as shown in FIG. 2. The center of the inlet-port and the center of the outlet-port indicate the center of the gravity in the figures drawn as the inlet port 4 and the outlet port 5. The center of the filter material 7 is the same point as the center of gravity when the filter material is assumed to be a uniform solid. It is preferable that both the distance 8 between the inlet port 4 and the center of gravity 7 and the distance between the outlet port 5 and the center of gravity 7 be 10 mm to 15 mm. If the inlet port and outlet port are not located in the positions as shown in FIG. 2, the flow of blood and blood components in the filter unpreferably tends not to be uniform.

The effective utilization rate of filter in the present invention indicates a ratio of the area of the filter actually used by filtering blood or blood components after filtration to the effective filtration area of the filter when the blood or blood components are filtered by the leukocyte-removing filter. The "effective filtration area of a filter" in the present invention indicates the area of the filter material of the leukocyte-removing filter through which blood can pass. "The area of the filter actually used after filtration" indicates the area of the leukocyte-removing-filter material through which blood actually passes when the blood is caused to flow through the filter of the flexible container. When blood or blood components pass through a filter under a constant pressure, the effective utilization rate of the filter is proportional to an amount of flow per unit time, i.e. a flow rate. Specifically, the effective utilization rate of the filter can be evaluated by the ratio of the filtration flow rate when a specific quantity of a liquid is filtered by using volume restriction boards to the filtration flow rate when the liquid is filtered without using the volume restriction boards. The filtration flow rate is measured as follows. Blood or blood components in a reservoir bag for blood before filtration is fed to and filtered through a leukocyte-removing filter, of which the thickness is restrained using volume restriction boards, under pressure by using a blood pump until the bag is emptied. In this instance, the period from the time when the blood or blood components reach the filter material on the inlet port side of the leukocyte-removing filter until the time when the reservoir bag for blood before filtration is emptied is measured as the filtration time.

The filtration flow rate V (ml/min) when using volume restriction boards can be determined by applying the weight W (g) of recovered blood or blood components, filtration time t (min), and the specific gravity d (g/ml) of the blood or blood components to the following equation.

$V=(W/d)/t$

The filtration flow rate $V_0$ (ml/min) when volume restriction boards are not used can be determined by applying the weight $W_0$ (g) of a blood or blood components when the blood or blood components are filtered using a leukocyte-removing filter with the same properties and the filtration time $t_0$ (min) to the following equation.

$V_0=(W_0/d)/t_0$

The effective utilization rate of a filter can be determined by substituting these values to the following formula.

Effective utilization rate(%)=$(V/V_0)\times 100$

This index is used also in examples described below.

EXAMPLES

The present invention will be explained in more detail by examples which are not intended to limit the present invention.

Example 1

An inlet port side flexible container having an inlet port of blood and an outlet port side flexible container having an outlet port of blood were prepared from a flexible sheet made of a polyvinyl chloride resin with Young's modulus of 10 N/mm$^2$ and a thickness of 0.4 mm, in which holes with a diameter equivalent to or larger than the inner diameters of the inlet port and outlet port were made at the locations to which the inlet port and outlet port of blood were to be welded, and tubes made of polyvinyl chloride with an inner diameter of 3 mm and an outer diameter of 4.2 mm, by welding at the inlet port and outlet port by high frequency welding, respectively. The inlet port and outlet port were welded by high frequency welding to the flexible container material so that the distances from the center of the filter to the center of the inlet port and the center of the outlet port are respectively 12 mm.

Sheets of nonwoven polyester fabric described below were laminated and used as a leukocyte-removing-filter material. A total of 34 sheets of non-woven fabric consisting four sheets of non-woven fabric (non-woven fabric (1)) having average fiber diameter of 12 μm and fiber density (metsuke) of 30 g/m$^2$, two sheets of non-woven fabric (non-woven fabric (2)) having average fiber diameter of 1.7 μm and fiber density (metsuke) of 66 g/m$^2$, 22 sheets of non-woven fabric (non-woven fabric (3)) having average fiber diameter of 1.2 μm and fiber density (metsuke) of 40 g/m$^2$, two sheets of non-woven fabric (2), and four sheets of non-woven fabric (1) were laminated in this order. The total thickness of the leukocyte-removing-filter material was 8.4 mm. The laminate made of these three types of nonwoven fabric prepared as described above was cut into a rectangle of 84 mm×104 mm. The flexible containers and the laminate of nonwoven fabric were layered in the order of the inlet port side flexible container, the laminate of nonwoven fabric, and outlet port side flexible container and welded by high frequency welding to form a leukocyte-removing filter with an effective filtration area of 65×85 mm$^2$. The thickness of the leukocyte-removing filter was 9.2 mm, the air permeability pressure drop was 500 Pa, and the effective filtration area was 55 cm$^2$.

The nonwoven fabric (2) and nonwoven fabric (3) were practically used after coating with a copolymer of N,N-dimethylaminoethyl methacrylate (hereinafter "DM") and 2-hydroxyethyl methacrylate (hereinafter "HEMA") at a DM/HEMA molar ratio of 3/97 by a known method. The amount of the coated copolymer was about 10 mg per 1 g of nonwoven fabric.

The leukocyte-removing filter was disposed between a reservoir bag for blood before filtration and a recovery bag of blood after filtration. An inlet-side tube connected with the reservoir bag for blood before filtration was connected with the inlet port of the leukocyte-removing filter, and an outlet-side tube connected with the recovery bag was connected to the outlet port of the leukocyte-removing filter. A polyvinyl chloride tube having an inner diameter of 3.0 mm and an outer diameter of 4.2 mm was used as the each tube. A Y-shaped tube was connected to the inlet side tube and a digital pressure gauge was installed via the tube. In addition, a blood pump for supplying blood under pressure was installed between the reservoir bag for blood before filtration and the Y-shaped tube connected to the a digital pressure gauge.

The configuration of the volume restriction boards facing the external surfaces of the inlet port side and the outlet port side of the leukocyte-removing filter was as follows. $3 \times 4$ cm$^2$ grooves were opened in a plane $17 \times 17$ cm$^2$ acrylic board to provide a structure by which the circumferences of the blood inlet-port side and the outlet-port side are not pressed. In addition, grooves with a width of 5 mm and a depth of 5 mm were formed along the tube at locations in which the tubes of the volume restriction boards come in contact, so that the tubes on the blood inlet-port side and outlet-port side may not be bent by the volume restriction boards. Otherwise flat board was used for the leukocyte-removing-filter side of volume restriction boards.

A leukocyte-removing filter was disposed and secured between these two volume restriction boards so that the space between the volume restriction boards is 10.2 mm (=[thickness of leukocyte-removing filter+1.0 mm]).

A concentrated erythrocyte product was prepared as follows. 56 ml of acid-citrate-dextrose (ACD)-A solution was added to 450 ml of human whole-blood. Within eight hours after blood collection, platelet-rich plasma was removed by centrifugation and 100 ml of Adenine-mannitol-saline (Adsol) was added as an erythrocyte preservation solution to obtain 300 ml of a concentrated erythrocyte product. The viscosity of the concentrated erythrocyte product was 10 mPa·s.

The leukocyte removal performance was evaluated by feeding and filtering the concentrated erythrocyte product to the leukocyte-removing filter using a blood pump under a pressure of 40 kPa. The concentrated erythrocyte product was continuously supplied to the leukocyte-removing filter using the blood pump until the reservoir bag for blood before filtration emptied. In this instance, the period from the time when the concentrated erythrocyte product reached the filter material on the inlet port side of the leukocyte-removing filter until the time when the reservoir bag for blood before filtration emptied was measured as the filtration time.

The leukocyte concentration in the concentrated erythrocyte product before filtration and the recovered concentrated erythrocyte were measured according to the following method.

600 µl of concentrated erythrocyte product was added to a TruCOUNT test tube containing a known number of fluorescent beads. 2,400 µl of LeucoCOUNT reagent was added to the test tube and gently mixed. The mixture was allowed to stand in a dark place at room temperature for 5 minutes. Ten TruCOUNT test tubes prepared in this manner were continuously measured using a flow cytometer ("FACSCalibur HG" manufactured by Nippon Becton Dickinson). The LeucoCOUNT reagent and TruCOUNT test tube of a LeucoCOUNT kit (manufactured by Nippon Becton Dickinson) were used. The leukocyte concentration in the concentrated erythrocyte product before filtration was $1 \times 10^7$ cells/ml.

The weight of recovered concentrated erythrocyte and the filtration time were measured to determine the filtration flow rate when using the volume restriction boards according to the above formula. The specific gravity d of the concentrated erythrocyte was 1.08 g/ml.

A concentrated erythrocyte product was filtered in the same manner as above by using a leukocyte-removing filter with the same properties as described above, except that a volume restriction board was not used. The weight of recovered concentrated erythrocyte and the filtration time were measured to determine the filtration flow rate when a volume restriction board was not used according to the above formula. The effective utilization rate of the leukocyte-removing filter was then determined.

Figure 3:
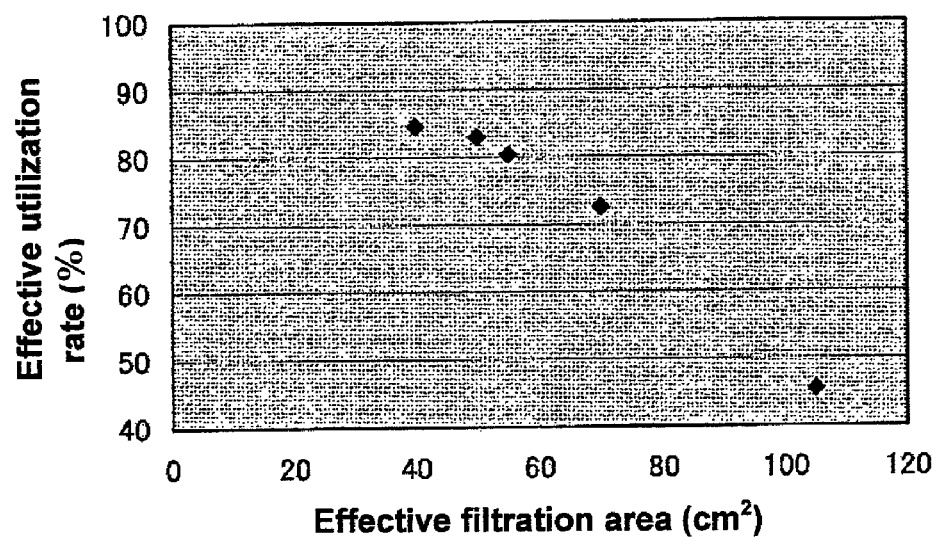
FIG. 3 is a graph showing the relationship between the effective filtration areas and the effective utilization rate of the leukocyte-removing filters in Examples 1 to 3 and Comparative Examples 1 to 2.
Figure 4:
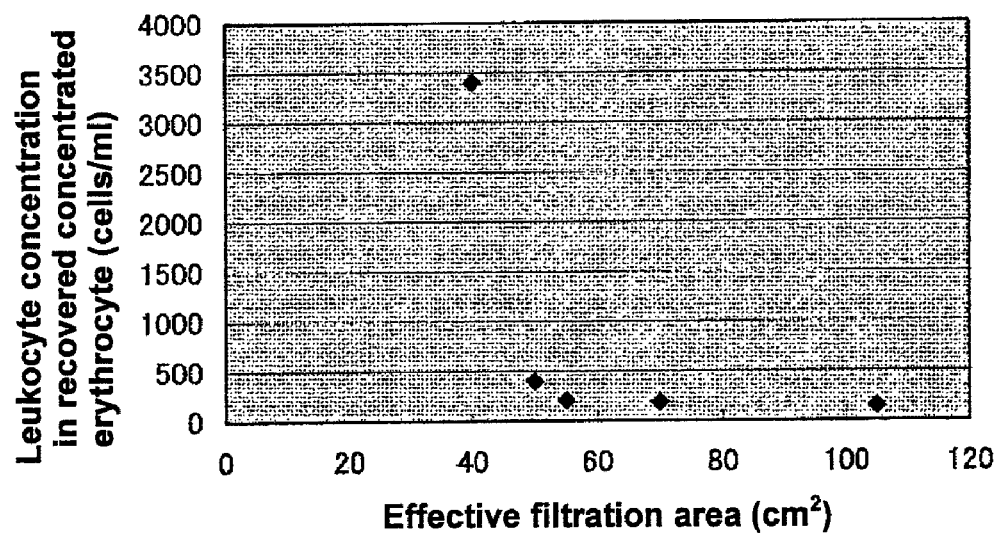
FIG. 4 is a graph showing the relationship between the effective filtration areas and the leukocyte concentration in recovered concentrated erythrocyte in Examples 1 to 3 and Comparative Examples 1 to 2.

The effective utilization rate of the leukocyte-removing filter and the leukocyte concentration in the recovered concentrated erythrocyte are shown in Table 1 and FIGS. 3 and 4.

Example 2

The same experiment as in Example 1 was carried out using a leukocyte-removing filter with the same configuration as that used in Example 1 and the same volume restriction boards as in Example 1, except that the effective filtration area of the filter was $7.3 \times 9.6 = 70$ cm$^2$ and the air permeability pressure drop was 393 Pa. The effective utilization rate of the leukocyte-removing filter and the leukocyte concentration of the recovered concentrated erythrocyte are shown in Table 1 and FIGS. 3 and 4.

Example 3

The same experiment as in Example 1 was carried out using a leukocyte-removing filter with the same configuration as that used in Example 1 and the same volume restriction boards as in Example 1, except that the effective filtration area of the filter was $6.2 \times 8.1 = 50$ cm$^2$ and the air permeability pressure drop was 550 Pa. The effective utilization rate of the leukocyte-removing filter and the leukocyte concentration of the recovered concentrated erythrocyte are shown in Table 1 and FIGS. 3 and 4.

Comparative Example 1

The same experiment as in Example 1 was carried out using a leukocyte-removing filter with the same configuration as that used in Example 1 and the same volume restriction boards as in Example 1, except that the effective filtration area of the filter was $5.5 \times 7.2 = 40$ cm$^2$ and the air permeability pressure drop was 688 Pa. The effective utilization rate of the leukocyte-removing filter and the leukocyte concentration of the recovered concentrated erythrocyte are shown in Table 1 and FIGS. 3 and 4.

The leukocyte concentration in the recovered concentrated erythrocyte was 3,400 cells/ml, indicating insufficient leukocyte removal as compared with other examples.

Comparative Example 2

The same experiment as in Example 1 was carried out using a leukocyte-removing filter with the same configuration as that used in Example 1 and the same volume restriction boards as in Example 1, except that the effective filtration area of the filter was $8.9 \times 11.9 = 105$ cm$^2$ and the air permeability pressure drop was 262 Pa. The effective utilization rate of the leukocyte-removing filter and the leukocyte concentration of the recovered concentrated erythrocyte are shown in Table 1 and FIGS. 3 and 4.

The effective utilization rate of the filter was 45.5%, confirming that the flow rate was slow due to low utilization of the effective filtration area of the filter in spite of the large area thereof as compared with other examples.

TABLE 1

|  | Comparative Example 1 | Example 3 | Example 1 | Example 2 | Comparative Example 2 |
|---|---|---|---|---|---|
| Effective filtration area (cm$^2$) | 40 | 50 | 55 | 70 | 105 |
| Effective utilization rate (%) | 84.6 | 83.0 | 80.4 | 72.6 | 45.5 |
| Leukocyte concentration in recovered concentrated erythrocyte (cells/ml) | 3400 | 400 | 210 | 190 | 150 |

As mentioned above, when a concentrated erythrocyte product was filtered under specific conditions using a leukocyte-removing filter satisfying conditions such as specific effective filtration area and the like shown in the examples as the present invention, a high effective utilization rate of the leukocyte-removing filter was achieved and, at the same time, the leukocyte concentration in the recovered concentrated erythrocyte could be reduced, whereas in comparative examples, the effective utilization rate of the leukocyte-removing filter was low and the leukocyte concentration in the recovered concentrated erythrocyte was high.

INDUSTRIAL APPLICABILITY

The method and device for filtering blood or blood components according to the present invention can reduce a concentration of leukocytes in a liquid after filtration to 1,000 cells/ml or less, effectively utilizing rate may be 70% or more, and the effective filtration area of the filter can be used effectively.

The method and device for filtering concentrated erythrocyte according to the present invention are useful for preparing concentrated erythrocyte product from which leukocytes are removed mainly for use in transfusion.

The invention claimed is:

1. A method for filtering blood or blood components, comprising providing a leukocyte-removing filter having a thickness of 9.0 mm to 9.4 mm, an air permeability pressure drop of 300 Pa to 700 Pa and effective filtration area of 50 cm$^2$ to 70 cm$^2$ which comprises a flat and flexible container having an inlet port and an outlet port and a sheet-like leukocyte-removing-filter material with a thickness of 8.2 mm to 8.6 mm disposed to divide the container into an inlet-port side chamber and an outlet-port side chamber, providing a pair of volume restriction boards disposed outside of the inlet port side external surface and the outlet port side external surface of the flexible container, having the distance between the volume restriction boards at the portion where the volume restriction boards facing each other sandwich the leukocyte-removing filter being in a range from [thickness of leukocyte-removing filter+0.5 mm] to [thickness of leukocyte-removing filter+2.5 mm], and filtering blood or blood components through the leukocyte-removing filter under a pressure of 30 kPa to 50 kPa while restraining the expansion of the flexible container occurring during filtration by means of the volume restriction boards.

2. The method according to claim 1, wherein the viscosity of blood or blood components is 5 mPa·s to 15 mPa·s.

3. The method according to claim 1, wherein the blood or blood components are a concentrated erythrocyte product.

4. The method according to claim 1, wherein the flat and flexible container has Young's modulus of 7 N/mm$^2$ to 13 N/mm$^2$ and a thickness of 0.2 mm to 0.6 mm.

5. The method according to claim 1, wherein the center of the inlet port and the center of the outlet port provided in the flat and flexible container are located on an intersection of a plane which is perpendicular to the filter material and passes through the center of the filter material, and the inlet-port side external surface or the outlet-port side external surface, the straight line which connects the center of the inlet-port and the center of the outlet-port passes through the center of the filter material, and the center of the inlet-port and the center of the outlet-port are respectively 10 mm to 15 mm apart from the center of the filter material.

6. The method according to claim 1, wherein the volume restriction boards cover 80% to 100% of the effective filtration area of the leukocyte-removing filter.

7. A device for filtering blood or blood components, comprising (a) a leukocyte-removing filter having a thickness of 9.0 mm to 9.4 mm, an air permeability pressure drop of 300 Pa to 700 Pa, and effective filtration area of 50 cm$^2$ to 70 cm$^2$ which comprises a flat and flexible container having an inlet port and an outlet port and a sheet-like leukocyte-removing-filter material with a thickness of 8.2 mm to 8.6 mm disposed to divide the container into an inlet-port side chamber and an outlet-port side chamber, and (b) a pair of volume restriction boards disposed outside of the inlet port side external surface and the outlet port side external surface of the flexible container, having the distance between the volume restriction boards at the portion where the volume restriction boards facing each other sandwich the leukocyte-removing filter being in a range from [thickness of leukocyte-removing filter+0.5 mm] to [thickness of leukocyte-removing filter+2.5 mm].

8. The device according to claim 7, wherein the flat and flexible container has Young's modulus of 7 N/mm$^2$ to 13 N/mm$^2$ and a thickness of 0.2 mm to 0.6 mm.

9. The device according to claim 7, wherein the center of the inlet port and the center of the outlet port provided in the flat and flexible container are located on an intersection of a plane which is perpendicular to the filter material and passes through the center of the filter material, and the inlet-port side external surface or the outlet-port side external surface, the straight line which connects the center of the inlet-port and the center of the outlet-port passes through the center of the filter material, and the center of the inlet-port and the center of the outlet-port are respectively 10 mm to 15 mm apart from the center of the filter material.

10. The device according to claim 7, wherein the volume restriction boards cover 80% to 100% of the effective filtration area of the leukocyte-removing filter.

11. The device according to claim 7, wherein a pair of the volume restriction boards is an integral structure with a U-shaped cross-sectional configuration.

12. The device according to claim 7, wherein a pair of the volume restriction boards is formed from two separate plates bonded in a secured or semi-secured state to maintain a certain space between them.

* * * * *